US00PP09936P

United States Patent [19]

Fuess

[11] Patent Number: Plant 9,936

[45] Date of Patent: Jun. 24, 1997

[54] CHRYSANTHEMUM PLANT NAMED 'EMPIRE GARNET'

[76] Inventor: Janet S. Fuess, 22 Country Club Dr., New York Mills, N.Y. 13417

[21] Appl. No.: 670,275

[22] Filed: Jun. 13, 1996

[51] Int. Cl.[6] ..... A01H 5/00

[52] U.S. Cl. ..... Plt./82

[58] Field of Search ..... Plt./76, 82

*Primary Examiner*—Howard J. Locker

*Attorney, Agent, or Firm*—Foley & Lardner

[57] ABSTRACT

A new and distinct cultivar of Chrysanthemum plant named Empire Garnet, characterized particularly by its red ray florets; fully double flowers; compact, rounded cushion habit; 4.0–4.5 cm capitulum diameter; natural season flower date of September 5 in New Hartford, N.Y.; and 7½ week flower response in light/shade programs.

1 Drawing Sheet

The present invention comprises a new and distinct cultivar of Chrysanthemum, botanically known as *Dendranthema grandiflora*, and referred to by the cultivar name Empire Garnet.

Empire Garnet is a product of a planned breeding program which had the objective of creating new chrysanthemum cultivars with formal decorative capitulum type, freely branching compact cushion habit, early flower response, rich red flower color, and an early flower response. Such traits in combination were not presnt in previously available commercial cultivars.

Empire Garnet was originated from a hybridization made by the inventor Janet S. Fuess in a controlled breeding program in New Hartford, N.Y. in 1990. The female parent was Empire Cheyenne, an orange-bronze decorative disclosed in U.S. Plant Pat. No. 8,973. The male parent of Empire Garnet was a dark red decorative cultivar identified as H87-23, a proprietary breeding line.

Empire Garnet was discovered and selected as one flowering plant within the progeny of the stated parentage by the inventor in September 1992 in a controlled environment in New Hartford, N.Y.

The first act of asexual reproduction of Empire Garnet was accomplished when vegetative cuttings were taken by the inventor from the initial selection in October 1991 in a controlled environment in New Hartford, N.Y. Horticultural examination of selected units initiated in 1992 has demonstrated that the combination of characteristics as herein disclosed for Empire Garnet are firmly fixed and are retained through successive generations of asexual reproduction.

Empire Garnet has not been observed under all possible environmental conditions. The phenotype may vary significantly with variations in environment such as temperature, light intensity, and day length, without, however, any variation in genotype. The following observations, measurements and comparisons describe plants grown in New Hartford, N.Y. under natural outdoor conditions which approximate those generally used in commercial practice.

The following traits have been repeatedly observed and are determined to be basic characteristics of Empire Garnet, which in combination distinguish this Chrysanthemum as a new and distinct cultivar:

1. Red ray florets each of which is approximately 2.2 cm long and 0.8 cm wide.
2. Fully double flowers, with no disc florets.
3. Average of 338 ray florets per flower.

4. Capitulum diameter of 4.0–4.5 cm.
5. 7½ week flower response in light/shade programs.
6. A natural season flower date of September 15 in New Hartford, N.Y.
7. Compact, rounded cushion habit.

Of the many commercial cultivars known to the present inventor, the most similar in comparison to Empire Garnet is Fiery Barbara. In comparison to Fiery Barbara, Empire Garnet has a slightly larger capitulum, flowers approximately 10 days earlier in natural season, and sizes up better. Empire Garnet is similar to Fiery Barbara with respect to excellent color retention, and its firm textured formal decorative flowers.

The accompanying color photographic drawing comprises a top perspective view showing typical flower and a foliage characteristics of Empire Garnet, with colors being as nearly true as possible with illustrations of this type.

In the following description, color references are made to The Royal Horitcultural Society Colour Chart. The color values were determined between 10:00 AM and 1:00 PM on Sep. 29, 1995 under 4,000 footcandles at New Hartford, N.Y.

Classification:

*Botanical.*—*Dendranthema grandiflora* cv. Empire Garnet.

*Commercial.*—Formal decorative garden mum.

INFLORESCENCE

A. Capitulum:
- *Form.*—Formal, decorative.
- *Type.*—Fully double.
- *Diameter across face.*—4.0–4.5.

B. Corolla of ray florets:
- *Color (General tonality from a distance of three meters).*—Red.
- *Color (upper surface).*—46B.
- *Color (under surface).*—35C.

C. Corolla of disc florets: No disc florets.

D. Reproductive organs:
- *Androecium.*—none.
- *Gynoecium.*—Present on ray florets; style 0.4 cm, bifurcated.

PLANT

A. General appearance:
- *Height.*—25–35 cm. when grown in an 8" pot.

B. Foliage:

*Color* (*upper surface*).—137B.

*Color* (*lower surface*).—139A.

Size and shape.—4.5–5.5 cm long, 3.5–4.0 cm. wide, 5-lobed.

It is claimed:

1. A new and distinct cultivar of Chrysanthemum plant named Empire Garnet, as illustrated and described.

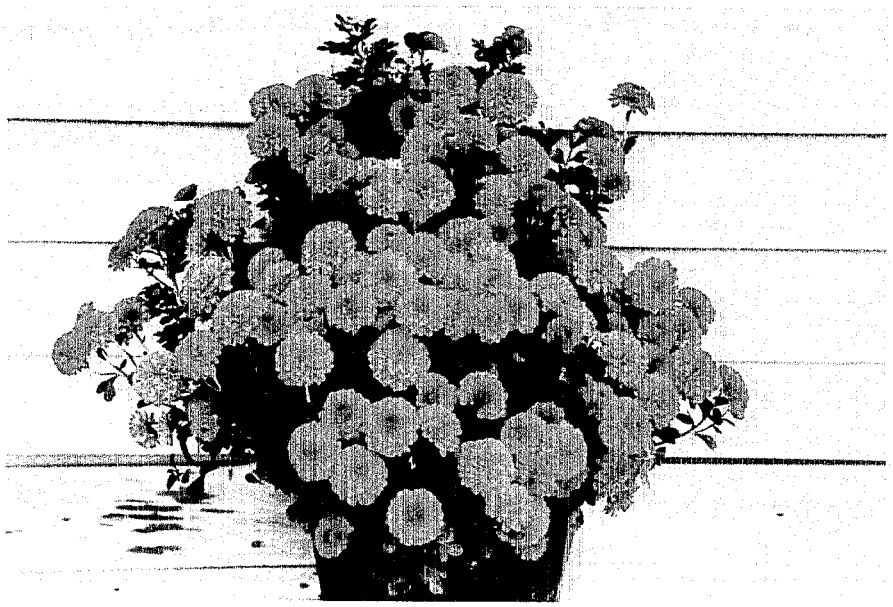

* * * * *